United States Patent [19]

Schmaltz et al.

[11] Patent Number: 5,449,372
[45] Date of Patent: Sep. 12, 1995

[54] TEMPORARY STENT AND METHODS FOR USE AND MANUFACTURE

[75] Inventors: Dale F. Schmaltz, St. Paul; Larry Walter, Maple Grove; Thomas Holman, Minneapolis; Gary Kostur, New Hope, all of Minn.

[73] Assignee: SCIMED Lifesystems, Inc., Maple Grove, Minn.

[21] Appl. No.: 715,164

[22] Filed: Jun. 14, 1991

Related U.S. Application Data

[63] Continuation-in-part of Ser. No. 594,121, Oct. 9, 1990.

[51] Int. Cl.⁶ ............................................. A61M 29/00
[52] U.S. Cl. ..................................... 606/198; 606/200; 604/104
[58] Field of Search ...................... 606/191, 198, 200; 623/1, 12; 604/104–109, 95

[56] References Cited

U.S. PATENT DOCUMENTS

| | | |
|---|---|---|
| 4,629,458 | 12/1986 | Pinchuk . |
| 4,650,466 | 3/1987 | Luther . |
| 4,739,762 | 4/1988 | Palmaz ............................ 623/1 |
| 4,998,539 | 3/1991 | Delsanti ........................... 606/194 |
| 5,002,560 | 3/1991 | Machold et al. .................. 604/104 |
| 5,180,368 | 1/1993 | Garrison . |

FOREIGN PATENT DOCUMENTS

| | | |
|---|---|---|
| 0321912A1 | 6/1989 | European Pat. Off. . |
| 0433011A1 | 6/1991 | European Pat. Off. . |
| 2580504A1 | 10/1986 | France . |
| 2652267A1 | 3/1991 | France . |
| 9010130.8 | 10/1990 | Germany . |
| 2020557 | 11/1979 | United Kingdom . |

Primary Examiner—Stephen C. Pellegrino
Assistant Examiner—William W. Lewis
Attorney, Agent, or Firm—Vidas, Arrett & Steinkraus

[57] ABSTRACT

A temporary stent for supporting a region of a vessel in a body comprising a composite stent portion and an actuator portion and methods for the use and manufacture thereof. The composite stent portion is comprised of an elongate perfusable vessel supporting portion adapted to be configurable between a reduced size for placement in the vessel and removal therefrom and an expanded size for structurally supporting the vessel and perfusable end portions connected to and forming ends of the vessel supporting portion and adapted to allow fluid flow therethrough. The composite stent portion is comprised of a plurality of resilient metallic wires coated with a polymeric material to provide stability for both lifting and maintaining a vessel. A method is disclosed for deployment of the composite stent to maintain vessel patency during occurrence of an intimal flap, vasoconstriction or vasospasm.

35 Claims, 6 Drawing Sheets

TEMPORARY STENT AND METHODS FOR USE AND MANUFACTURE

REFERENCE TO RELATED APPLICATION

This application is a continuation in part of Ser. No. 07/594,121, filed Oct. 9, 1990.

BACKGROUND OF THE INVENTION

This invention relates to devices known as stents which provide support to a vessel, such as a blood vessel, and in particular to stents that are both temporary and removable.

Obstructive coronary artery disease is one of most serious health problems facing our society today. This disease is the result of the deposit of fatty substances on the interior surface of the walls of the arteries. The build up or lesion of such deposits results in a narrowing of the diameter of the artery which restricts the blood flow through the artery. This condition wherein the artery is narrowed is known as stenosis. The lesion may form in any part of the artery and in some instances the deposits may form at the intersection between two arteries, that is, where the section where the two arteries form a generally "Y" configuration (e.g. bifurcate, trifurcate, and so on).

There have been significant developments of the treatment of such obstructive coronary disease in the recent past. Coronary artery bypass graft surgery is often used to treat this disease. Bypass surgery, however, has the disadvantage that it is extremely invasive and traumatic to the patient. Some of the recent developments provide a less invasive and less traumatic alternative to bypass surgery. Two of these recent developments are known as angioplasty and atherectomy procedures.

Angioplasty is a procedure in which a balloon is positioned on the inside of the artery at the site of the lesion and expanded in order to compress the materials at the lesion and thus open the restricted area in the artery. In this procedure, an elastic balloon is attached to one end of a small diameter flexible catheter which includes means for inflating the balloon from the other end of the catheter. The catheter is maneuvered through the patient's vessels to the site of the lesion with the balloon in uninflated form. When the uninflated balloon is properly positioned at the lesion, the balloon is then inflated to dilatate the restricted area.

Atherectomy is a procedure in which a small cutting tool is attached to the end of a small diameter flexible catheter and maneuvered through the patient's arterial system to the site of the lesion in the diseased artery. When the cutting tool is properly positioned, the tool is used to cut and remove the deposits from the surface of the diseased artery.

Although these two procedures provide less traumatic alternatives to bypass surgery, they are not without risk. It is possible that following procedures such as angioplasty or atherectomy the artery or blood vessel may collapse or be susceptible to constriction. In some instances it may also be necessary to abort or "bail-out" procedures such as angioplasty or atherectomy due to some type of unexpected complication.

In these situations it is necessary to maintain the integrity of the region of the artery until the artery is repaired or stabilizes. That is, following some angioplasty or atherectomy procedures or in a "bail-out" situation, it may be necessary to provide support to a artery or blood vessel on a temporary basis while there is an immediate risk that the region may collapse. This support must be provided until the region is repaired or stabilized. To provide this support, a device known as a stent may be installed at the desired region. A stent is a device which is used to hold or maintain the diameter of the artery or vessel.

Although some stents are available in the art, these are generally of the type intended for permanent use. This type of permanent stent is implanted in a patient's vascular system and remains in place after the procedure or operation. Such permanent types of stents are shown, for example, in U.S. Pat. Nos. 4,913,141, 4,878,906, 4,856,516 and 4,820,298. These permanent type of stents may not always be desired for the situations described above. First, it may be unnecessary and even undesirable to install a permanent device when only temporary support is needed. Further, these permanent type of stents may require a relatively complicated procedure to install. Further, use of permanent stents results in extended hospital observation and recovery time. Additionally, a complement of drug therapies are required in order to offset the bioreaction resulting in thrombus formation or smooth muscle cell proliferation on the stent surface. These drug therapies may be required for a significant period of time until new normal endothelial cells have formed. In situations such as a "bail-out it is desirable for the physician to have the ability to quickly maneuver the stent to the desired location and quickly and easily place the stent in its operating mode.

A temporary stent on the other hand may be particularly useful in situations where it is intended to be used in the patient only for several minutes or days and then removed. For example, use of a temporary stent in a bail-out situation will enable the physician to defer a more complicated procedure until a patient's condition is more stable, or in some cases eliminate further procedures by resecuring the vessel geometry which allows near normal blood flow.

A temporary stent may have particular usefulness in situations such as when an intimal flap is encountered or during occurrrences of vasoconstriction or vasospasm or in situations in which there is a potential for such conditions to occur such as following angioplasty. An intimal flap occurs when a portion of the vessel wall partially or completely tears off and hangs down into the blood flow path. An intimal flap may occur during or after an angioplasty procedure. If the flap is large, it may entirely occlude the vessel lumen. The flap may heal itself if it can be maintained in place against the vessel from which it tore.

Vasoconstriction or vasospasm also may occur during or after angioplasty. Vasoconstriction or vasospasm in many cases may accompany the occurrence of an intimal flap, but in many other cases, vasoconstriction or vasospasm may occur independent of an intimal flap. During vasoconstriction or vasospasm, muscles around the vessel contract and can partially or completely occlude the vessel. If the vessel can be maintained open, vasoconstriction or vasospasm may cease after a period of time. Medicines may be administered to treat the vasoconstriction or vasospasm. Whereas a small force may be sufficient to maintain an intimal flap against the vessel wall and maintain blood flow, a significantly greater force would usually be needed to keep a vessel open during an episode of vasoconstriction or vasospasm.

It is essential that a temporary stent be relatively easy to both install and remove. Since the temporary stent remains in place for a period of time, it is important that the temporary stent not block the flow of blood through the vessel. That is, the blood must be able to travel through the vessel in which the temporary stent is installed while the stent is in place. Further, since the lesions often occur at the intersection of two vessels, in order to position the temporary stent it is may be necessary to place the stent across the intersection. Therefore, it is critical that the stent provide a flow path radially as well as axially or longitudinally. This arrangement will allow blood flow to both of the intersecting arteries.

It is also desirable to have the ability to deliver medicines to the vessel either upstream or downstream of temporary stent while the stent is in place.

Since the temporary stent will be removed after a period of time, it is important that the temporary stent not permanently adhere to the inner walls of the vessel in which it is placed. In addition, a temporary stent should have no tendency, or only a minimal tendency, to cause clotting.

Accordingly, it is an object of the present invention to provide a stent that may be placed temporarily in a patient's vascular system and which is readily removable.

SUMMARY OF THE INVENTION

The present invention relates to a temporary stent for supporting a region of a vessel in a body comprising a composite portion and an actuator portion and methods for the use and manufacture thereof. The composite stent portion is comprised of an elongate perfusable vessel supporting portion adapted to be configurable between a reduced size for placement in the vessel and removal therefrom and an expanded size for structurally supporting the vessel. The composite stent portion is comprised of a plurality of resilient metallic wires coated with a polymeric material to provide stability for both lifting and maintaining a vessel.

With this arrangement, the temporary stent may be positioned in the desired region and may be used to maintain vessel patency during the occurrence of an intimal flap, vasoconstriction, vasospasm, or other conditions that occlude the vessel lumen or when there is a potential that such conditions may occur such as following angioplasty.

DETAILED DESCRIPTION OF THE PRESENTLY PREFERRED EMBODIMENTS

Figure 1:
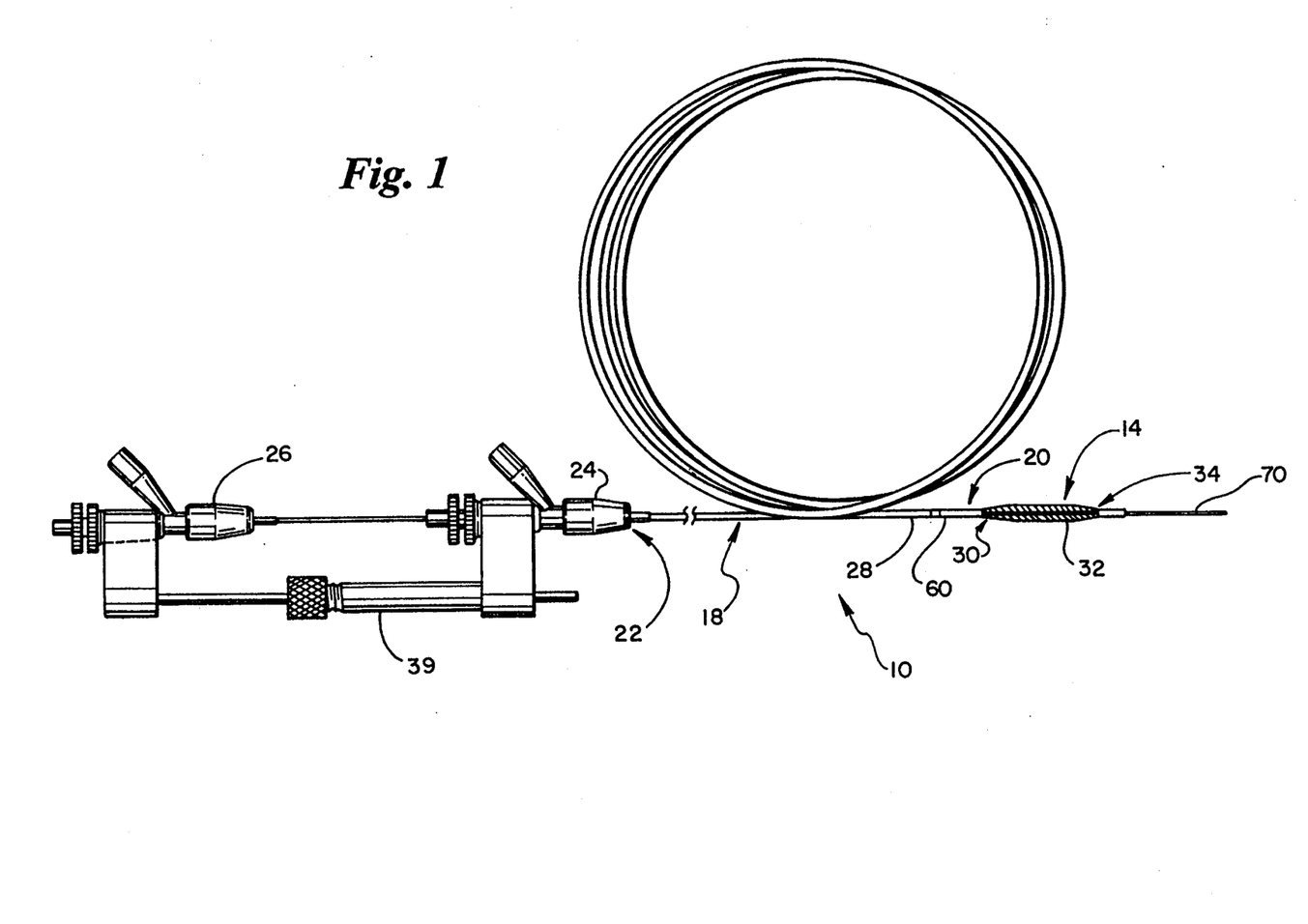
FIG. 1 depicts a first embodiment of the present invention.

Referring to FIG. 1, there is depicted a first embodiment of the present invention. The embodiment of FIG. 1 is a temporary stent 10 which can be placed in the vascular system of a patient after a procedure such as angioplasty, atherectomy or other interventional therapies. Although the temporary stent 10 is particularly useful in procedures involving blood vessels, it may be used in other fluid carrying vessels in the patient's body. As used herein, the term "vascular system" refers to a vessel for conveying body fluids. The temporary stent 10 is intended for placement in a vascular system for limited durations of time from several minutes to up to several days.

In the embodiment of the invention depicted in FIG. 1, the temporary stent 10 includes a perfusable stent portion 14 and an actuator portion 18. The stent portion 14 is connected to a distal end 20 of the actuator portion 18. When the temporary stent 10 is being used in a patient, the actuator portion 18 extends proximally from its connection to the stent portion 14 through the vascular system and out of the body of the patient. In one embodiment, the proximal end 22 of the actuator portion 18 extends out the body of the patient is connected to one or more, for example two, manifolds 24 and 26.

The stent portion 14 is expandable and contractable so that it can be positioned in the vascular system at the specific location where needed and then expanded to an appropriate size (i.e. approximately the same diameter as the vessel in the region where placed) thus supporting that vascular region. When in its expanded configuration, the stent portion 14 provides support to the vascular walls thereby preventing constriction of the vascular region in which it is located and maintaining the vascular lumen open.

The construction and materials for the stent portion 14 should provide that the stent be perfusable, i.e. it should allow blood flow therethrough both in the axial direction of the vessel to maintain blood flow through the region in which the stent is located as well as in the radial direction so that any vessels that branch off from the region of the vessel into which the stent portion is placed will not be occluded. Thus, the stent portion 14 should be relatively transparent to blood flow in order to maintain vascular function while at the same time providing support for the vessel walls in the region where it is located.

Expansion and contraction of the stent portion 14 inside the patient's body may be accomplished from outside of the patient's body by means of manipulation of the actuator portion 18 from the proximal end 22 thereof which is located outside the patient's body. In this embodiment, the actuator portion 18 comprises a first elongate member 28 that connects to a proximal end 30 of the stent portion 14 and a second elongate member 32 that connects to the distal end 34 of the stent portion 14. Relative movement of the first elongate member 28 and the second elongate member 32 causes expansion and contraction of the stent portion 14, as explained in more detail below. The distal end 20 of the actuator portion 18 remains in place in the body during the period of time that the stent portion 14 is in place in the vascular system and during this time the proximal end 22 of the actuator portion 18 extends out of the patient's body. At the proximal end of the actuator portion 18, the first elongate member 28 terminates at a manifold 24 and the second elongate member 32 terminates at the manifold 26. In one embodiment, these manifolds include hemostatic valves and Y-connecters for administering fluids, such as medicines through these manifolds, as described below.

In a preferred embodiment, the stent portion 14 is comprised of a braid made of a plurality of helically wound wires forming an elongated hollow tube. Typically, half of the wires forming this tube will be wound in one helical direction and the other half will be wound in the opposite helical direction and interwoven with the first half. Braiding of these wires provides for an elongated, expandable hollow tube that can, in a preferred embodiment, increase in diameter when the ends of the hollow tube are moved closer relative to each other and decrease in diameter when the ends of the hollow tube are move apart relative to each other. The ratio by which the stent portion expands depends upon the spacing between adjacent wires that make up the braid as well as the cross sectional dimensions of each of the individual wires.

The stent portion 14 may be provided in a wide range of sizes and stiffnesses to meet the requirements for use with different lesions, flaps, or vasoconstrictions in a patient's vascular system. The stent portion 14 is constructed to be flexible enough to traverse its way to the region of the vascular system where it is to be located and expanded to provide support for the region of the vascular system, such as the site of previous angioplasty or other treatment.

The stent portion 14 terminates in a distal end 34. Located inside the hollow tube of the stent portion 14 is the second (or inner) elongate member 32. The second elongate member 32 is connected to the distal end 34 of the stent portion 14, as explained below. The second elongate member 32 extends proximally from its connection to the distal end 34 of the stent portion 14, through the hollow tube of the stent portion 14, and through an inner lumen of the first elongate member 28 to the proximal end thereof. In accordance with this embodiment, relative movement between the first elongate member 28 and the second elongate member 32 causes corresponding movement of the proximal end 30 and distal end 34 of the stent portion 14 thus in turn causing expansion or contraction of the diameter of the elongate hollow tube of the stent portion 14.

Figure 2:
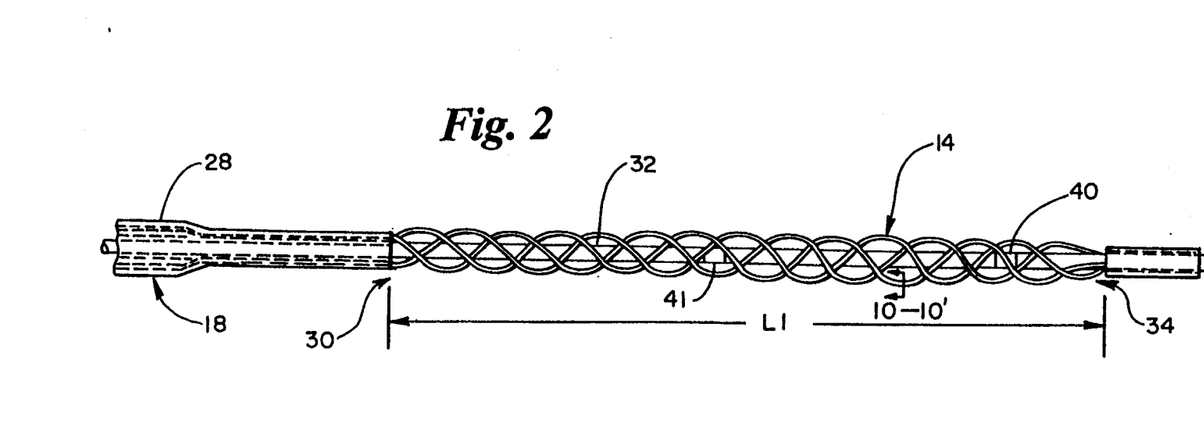
FIG. 2 shows a distal portion of the embodiment depicted in FIG. 1 with the stent portion in a reduced contracted configuration.
Figure 3:
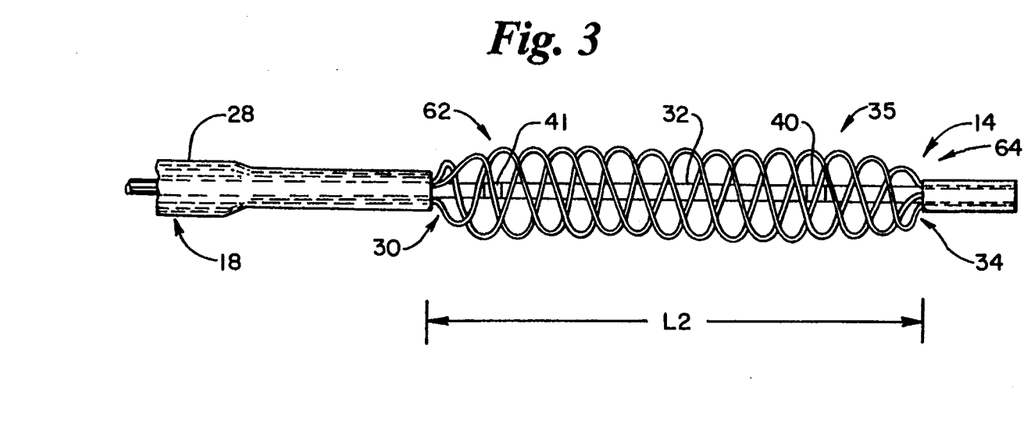
FIG. 3 shows a distal portion of the embodiment depicted in FIG. 1 with the stent portion in an expanded configuration.

In FIG. 2, the temporary stent 10 is depicted in its constricted configuration with the elongate hollow tube of the stent portion 14 having a reduced diameter. In this configuration, the second elongate member 32 extends distally from the first elongate member 28 so that the length of the stent portion 14 is L1. In FIG. 3, the second elongate member 32 is positioned at a location more proximate relative to the first elongate member 28 than in FIG. 2 (i.e., in the direction of arrow 35) causing the length of the stent portion 14 to be equal to L2 (L2 being less than L1). In the process of moving proximally relative to the first elongate member 28, the second elongate member 32 causes the proximal and distal ends 30 and 34, respectively, of the stent portion 14 to move relatively closer together thus causing the diameter of the elongate hollow tube of the stent portion 14 to expand to a dimension suitable for supporting a region of the vascular system. The temporary stent 10 can be maintained in this expanded configuration by fixing the proximal ends of the first and second elongate members 28 and 32 for the duration of the time that the temporary stent 10 is maintained in the vascular system. This may be done by attaching a clamp 39 or similar device to the proximal ends of the first elongate member 28 and the second elongate member 32 at the manifolds 24 and 26. These two elongate members can be later disengaged from each other to permit reducing the diameter of the temporary stent 10 for removal thereof from the body. In alternative embodiments, the first and second elongate members may be fixed by means of an actuator manifold, as described below.

In order to provide a means by which the position of the temporary stent 10 in the body of the patient can be determined, one or more radiopaque markers, e.g. 40 and 41 may be located on a distal region of the stent, for example on a distal region of the second elongate member 32. These markers may be bands of radiopaque materials such as platinum, tantalum, gold, tungsten or a tungsten-iridium alloy.

Figure 11:
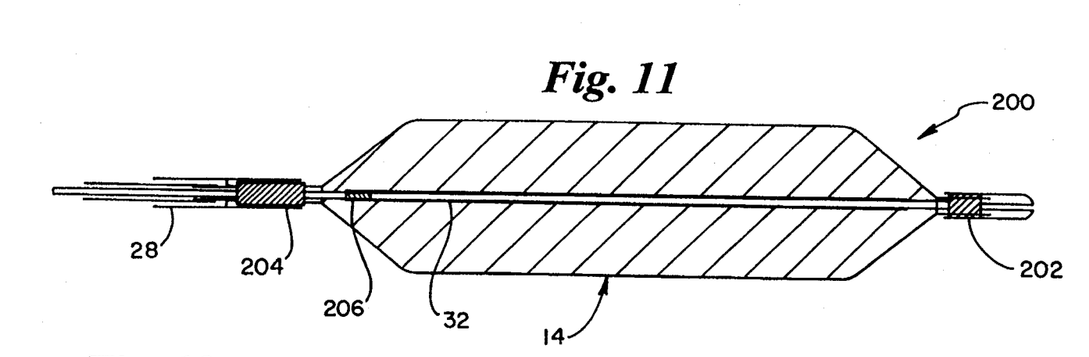
FIG. 11 is a longitudinal sectional view of a distal portion of another embodiment of the present invention.

Referring to FIG. 11, there is illustrated a distal portion of a most preferred embodiment 200 for incorporating radiopaque markers for use in an embodiment of the temporary stent. In this embodiment, there are three radiopaque markers associated with the distal portion of the temporary stent. A first marker 202 is located at or adjacent to a distal end of the stent portion 14. A second marker 204 is located at or adjacent to a proximal end of the stent portion 14. By means of these two markers 202 and 204, the length of the stent portion 14 can be determined during expansion and contraction. A third marker 206 is fixed to the second elongate member 32 in the region corresponding to the stent portion 14. Accordingly, by observing the position of the third marker 206 relative to the first and second markers 202 and 204, it is possible to obtain continuous feedback of the stent deployment during expansion and contraction. In a preferred embodiment, the third marker 206 is approximately adjacent to the second marker 204 when the stent portion is fully expanded and is approximately just proximal of the midline of the stent portion 14 when the stent portion 14 is contracted. In the preferred embodiment, the markers are made of platinum with 10% iridium.

In a most preferred embodiment, the markers are formed of wire that is wound around the proximal and distal ends of the braid and also serve the function of securing the proximal end of the braid to the first elongate member 28 and the distal end of the braid to the second elongate member 32. In the preferred embodiment, the braid is pulled down on a mandrel and the marker wire is coil wound around the ends of the braid. Then, the coils are clipped and brazed. In this manner, the braid is both secured to the catheters elongate member and markers are provided. Instead of brazing, the markers may be secured to the elongate members by means of welding, soldering, adhesives, or other means. The third marker, i.e. the marker located on the inner catheter 54, may be installed similarly except that it will not be connected to the braid.

Figures 4, 6:
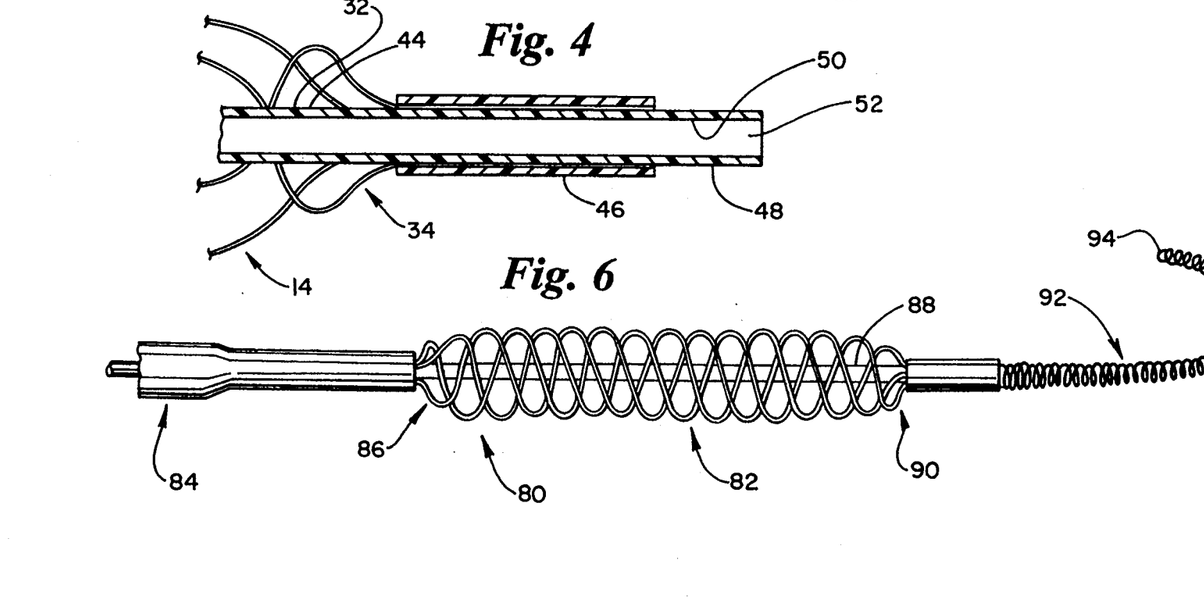
FIG. 4 is a longitudinal sectional view showing a portion of the embodiment depicted in FIG. 1.
FIG. 6 depicts a distal portion of another embodiment of the present invention.

Referring to FIG. 4, there is depicted a longitudinal cross section of the distal end of the second elongate member 32. In this embodiment, the second elongate member 32 is an inner catheter 44. As depicted in FIG. 2, the distal end 34 of the stent portion 14 surrounds an outside wall of the inner catheter 44. A collar 46 surrounds and affixes the distal ends of the wires that make up the braid of the stent portion 14 to the distal end of the inner catheter 44 (i.e. first elongate member 32). The collar 46 may be made of a balloon tubing polyolefin or other ultra-thin wall polymers. The collar 46 may be heated to fuse to the outer wall of the inner catheter 44 or connected thereto by an adhesive or other suitable means. In this manner, the distal end 34 of the stent portion 14 may be securely fixed to the inner catheter 44 suitably for the duration of the use of the temporary stent 10. A distal tip 48 of the temporary stent 10 is formed of an extension of the inner catheter 44 distally past the collar 46. This extension may be approximately 0.25 cm. This distal end may have an outer diameter of approximately 0.039 inches. The inner catheter 44 has a lumen 50 therewithin that communicates with an opening 52 at the distal tip 48.

Figure 5:
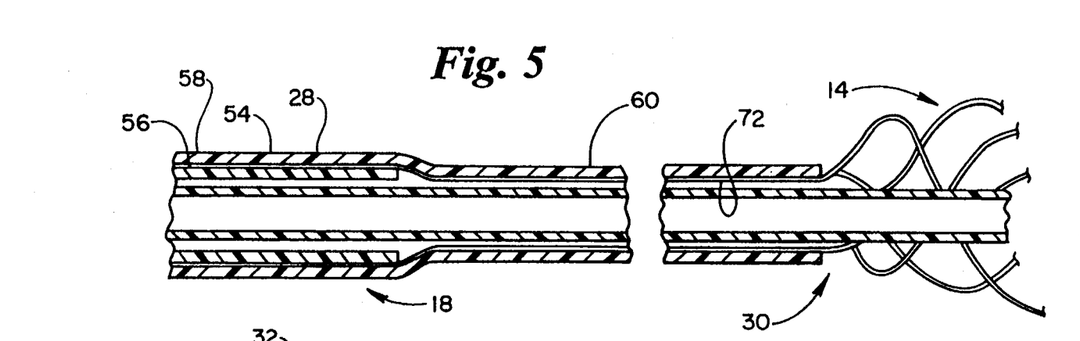
FIG. 5 is a longitudinal sectional view showing a portion of the embodiment depicted in FIG. 1.

Referring to FIG. 5, there is a longitudinal sectional view depicting a portion of the proximal end 30 of the stent portion 14 and the actuator portion 18 and specifically the connection of the proximal end 30 of the stent portion 14 to the first elongate member 28 of the actuator portion 18. In this embodiment, the first elongate member 28 is an outer catheter 54. As shown in FIG. 5, the outer catheter 54 includes an inner tubular layer 56 and an outer tubular layer 58 that is concentric with the inner tubular layer 56. The outer diameter of the outer catheter 54 would be approximately close to, but may be slightly larger than, the contracted diameter of the stent portion 14. Thus, for coronary applications, the outer catheter 54 may have an outer diameter of approximately 0.039 inches, and for peripheral applications the outer catheter 54 may have a diameter of approximately 2.10 mm. The length of the outer catheter 54 could be made to various sizes to be suitable for different treatment sites. For coronary applications, the length of the outer catheter 54 would be approximately 175 cm, for example.

In this embodiment, the proximal end 30 of the stent portion 14 is secured between the inner and outer concentric tubular layers 56 and 58 by extending the wires of the braid proximally between these concentric layers. The concentric tubular layers 56 and 58 and the wires of the braid of the stent portion 14 may be bonded together by an appropriate adhesive or by heating. A frictional fit may also be suitable. Preferably, the wires of the braid terminate proximally at the proximal end of the first elongate member 28. Alternatively, the wires of the braid may extend the entire length proximally to the proximal end of the first elongate member 28 or the wires of the braid of the stent portion 14 may extend only a short distance or an intermediate distance proximally between the concentric tubular layers 56 and 58.

In this embodiment, the inner tubular layer 56 terminates a distance proximally from the distal end of the outer tubular layer 58. This enables the outer catheter 54 (i.e., first elongate member 18) to be reduced in diameter in the distal region thereof forming a necked down portion 60 to facilitate positioning the temporary stent 10 in a region of the vascular system. The necked down portion 60 of the outer catheter 54 may be approximately 3 to 30 cm in length.

Referring again to FIG. 3, when the stent portion is in its expanded configuration, the proximal 30 and distal 34 ends of the stent portion 14 will assume a proximal and distal truncated conical profile regions 62 and 64. These truncated conical profile regions 62 and 64 taper from a narrow dimension where the wire braid is affixed to the actuator portion 18 proximally and distally (i.e., first and second elongate members 28 and 32) up to the expanded diameter of the stent portion 14. These regions 62 and 64 may be linearly tapered, but a non-linear taper may also be provided. The type of taper depends upon the type of braiding method used. Because the diameter of the second elongate member 32 is less than the diameter of the first elongate member 18, the distal tapered region 64 may not correspond exactly in size or slope to the proximal tapered region 62. In both the proximal tapered region 62 and the distal tapered region 64, the braiding method used preferably provides for relatively large distances between adjacent wires to provide correspondingly large openings around and through the plurality of wires at the ends of the stent portion 14 to facilitate blood flow therethrough.

In this embodiment, the temporary stent 10 may be positioned in the vascular region over a guidewire 70 through the lumen 50 of the inner catheter 44. The guidewire 70 may be a standard guidewire suitable for the region of the vascular system into which the stent will be located. According to this embodiment, the guidewire 70 is positioned in the vascular system across the region where it is desired to install the temporary stent 10. The guidewire 70 may be positioned by standard procedures. The diameter of the lumen 50 of the inner catheter 44 is of a sufficient size to allow the stent portion 14 to be advanced in the vascular system over the guidewire 70. The temporary stent 10 including the stent portion 14 and the distal end of the actuator portion 18 is advanced over the guidewire 70. The lumen 50 of the inner catheter may be compatible with 0.014, 0.016, or 0.018 guidewires for coronary applications and with up to 0.038 guidewires for peripheral applications.

Alternatively, the temporary stent 10 could be located in the vascular region by guiding it through a separate catheter (e.g. a delivery catheter) large enough to contain the temporary stent 10 in its contracted configuration.

For coronary applications, the stent portion 14 of this embodiment is expandable from a size of approximately 1.25 mm or less to up to approximately 4.0 mm. When used for peripheral applications, the stent portion 14 of the temporary stent 10 may have a contracted diameter of less than approximately 2.0 mm and an expanded diameter of up to approximately 6.0 mm. The length of the stent portion 14 is approximately 2.5 to 5 cm when in its most extended position (i.e. when the diameter of the stent portion 14 is in its contracted configuration). When the diameter of the stent portion is in its expanded configuration, the length of the stent portion is somewhat less, e.g. approximately 1.5 to 3.5 cm.

In a most preferred embodiment, the stent portion is provided in two alternative lengths: 25 and 40 mm. These dimensions refer to the length of the stent portion when it is deployed to support a portion of a vessel, i.e. in the expanded configuration.

In this embodiment, fluids such as medicines may be introduced to the vascular system via the lumen 50 of the inner catheter 44 as well as through a lumen 72 of the outer catheter 54 around the inner catheter 44. Medicines introduced via the inner catheter 44 will enter the vascular system at the distal end 48 of the stent portion 14 via opening 52. In this embodiment, sufficient space is provided in the lumen 72 of the outer catheter 54 around the inner catheter 44, so that a second passageway for the introduction of fluids such as medicines to the vascular system is also provided. Medicines introduced via the lumen 72 of the outer catheter 54 will enter the vascular system at the proximal end 30 of the stent portion 14. In this manner, the attending physician has the choice of selecting the point of entry for medicines administered e.g., either upstream or downstream of the stent portion 14. For instance, medicines, such as non-thrombogenic drugs, can be administered upstream of the stent portion 14 where they would be most effective in the region of the stent portion 14.

To remove the temporary stent 10, the stent portion 14 is first contracted from its expanded configuration to a reduced configuration. To do this, the first elongate member 28 is moved proximally relative to the second elongate member 32 thereby drawing down the diameter of the stent portion 14 to a size to facilitate removal from the vascular system. The wires of the stent portion 14 should smoothly peel from the vessel wall causing no or only minimal trauma. It is not necessary that the stent portion 14 be drawn down entirely to its completely reduced size. It is sufficient that the stent portion 14 is drawn down sufficiently to disengage the inner walls of the vascular region and to be of a size sufficiently small to traverse the vascular system out of the body. Then, after the stent portion 14 is in a reduced configuration it may be removed from the vascular system by drawing it out by means of the attached actuator portion 18.

The inner catheter 44 of the elongate member 14 has a geometry and is comprised of a material to provide for flexibility, tracking, axial compressive and tensile strength and rigidity for actuation of the stent portion 14. In a most preferred embodiment, the inner catheter 44 of the elongate member 14 is comprised of a thin-walled polyimide. Alternatively, the inner catheter 44 may be a polycarbonate, polyester or PET (high modulus polymer) tube. Such materials provide for the desired properties.

A lubricious coating may be utilized on the inner catheter 44. The lubricious coating may be a hydrophilic material, paralyene, teflon, or silicone. Such a coating may be utilized on either the inner or the outer surfaces of the inner catheter 44 or both. A lubricious coating on the inner surface of the inner catheter 44 facilitates over-the-wire movement of the temporary stent. A lubricious coating on the outer surface of the inner catheter 44 provides for low friction with the outer catheter 54 for good deployment and actuation of the stent portion 14.

The outer catheter 54 of the elongate member 14 should also have a geometry and should be comprised of a material to provide for flexibility, tracking, axial compressive and tensile strength and rigidity for actuation of the stent portion 14. In a most preferred embodiment, the outer catheter is made of polycarbonate. Alternatively, the outer catheter may be comprised of a thin-walled polyimide, polyester or PET (high modulus polymer) tube.

A lubricious coating may also be utilized on the outer catheter 54. The lubricious coating may be a hydrophilic material, paralyene, teflon, or silicone. Such a coating may be utilized on either the inner or the outer surfaces of the outer catheter 54 or both. A lubricious coating on the inner surface of the outer catheter 54 provides for low friction with the inner catheter 44 for good deployment and actuation of the stent portion 14. A lubricious coating on the outer surface of the outer catheter 54 facilitates positioning of the temporary stent in the patient's vascular system.

In an alternative embodiment of the present invention, the inner catheter 44 is comprised of a $0.021 \times 0.028$ inch polymeric tubing. The tubing used may be a blended Poly-Ethylene comprised of High Density Polyethylene (HDPE) and Low Density Poly-Ethylene (LDPE). Alternatively, the inner catheter 44 may also be constructed of Poly-Propylene, TPFE teflon or TPX. (TPX is a trade name for the Methyl Methylpentene Copolymer manufactured by Mitsui Plastics, Inc. and distributed from White Plains, NY). The use of TPX enables the stent to be used for ultrasound imaging of the vessel that is being supported by the stent because the acoustical properties of this polymer match to that of water and blood.

Referring to the first elongate member 28, the inner tubular layer 56 may be constructed of the same combination of polymers described for the inner catheter 44. The inner tubular layer 56 may terminate 3 to 30 cm proximally from the proximal end 30 of the stent portion 14. This provides for the ability to reduce the section of the outer layer 58 by way of a drawing (or necking operation) on the outer layer 58. The size for this inner tubular layer 56 of the first elongate member 28 is $0.033 \times 0.039$ inch.

The outer tubular layer 58 of the first elongate member 28 may also be constructed of blended HDPE-LDPE, or polypropylene. The dimensions of the outer tubular layer 58 of the embodiment may be $0.045 \times 0.053$ inches in the proximal section of the first elongate member 28 extending from the manifold 24 at the proximal end to approximately 3 to 30 cm from the proximal portion 30 of the stent portion 14. From this point distally, the outer tubular layer 58 may be reduced to $0.039 \times 0.045$. This may be accomplished by a necking or drawing operation which is achieved by pulling the tube through a heated die and allowing the plastic to reflow.

The inner dimension of the outer tubular layer 58 as well as the distal necked region 60 is adjusted accordingly for a 3.0 or 3.5 mm stent as may be seen to accommodate the wire of greater thickness. Since the outer diameter of the inner tubular layer 58 is 0.039 inches the placement of the braid on top of this layer, i.e. in the lumen 72, adds a factor of four times the wire thickness to the profile of the device prior to installation of the outer tubular layer 58. It is therefore apparent that the inner diameter of the outer tubular layer 58 should be adjusted to a minimum of 0.047 inches for the 3.0 mm and 3.5 mm versions. The tubing dimension may then be adjusted for the outer tubular layer to 0.055.

The stent portion 14 is comprised of a composite system that provides a consistent geometry during repeated expansions and contractions. In a most preferred embodiment, the stent portion has a geometry comprised of a uniform cylindrical middle portion with abrupt cone shaped geometries at the distal and proximal ends. This geometry minimizes constriction or impedance of the blood flow. The cone shaped regions at the distal and proximal ends have minimal lengths and preferably form an angle from the axial direction greater than 45 degrees. In a most preferred embodiment, the length of the stent portion is approximately 25 mm when in the expanded configuration.

In a most preferred embodiment, the stent portion is formed of a composite braid. The composite braid is formed of a resilient metal alloy wire coated with a polymeric coating. In the most preferred embodiment, the wire used for the composite braid is a heat treatable cobalt-chromium-nickel-molybdenum based alloy, such as Elgiloy or MP35N. In a most preferred embodiment, the Elgiloy wire used in the construction of the stent portion 14 is a round wire having a diameter of approximately 0.002 to 0.0025 inches. In one embodiment, the Elgiloy wire is treated to cause a metallurgical phase change so that the wire assumes a set shape to which it will have a tendency to resiliently resume. With Elgiloy wire, this phase change may be obtained by methods that are well known in the art and include steps of cold working and then heat treating the wire in the desired configuration to approximately 900 to 1000 degrees Fahrenheit. Other heat treatable alloys such as a stress relieved stainless steel could be utilized. Wire of other dimensions may also be used. Preferably, the Elgiloy wire is formed into a braid of a size corresponding to the radially expanded size. Then, the wire is heat treated with the braid of the stent portion in the expanded configuration thereby imparting the desired memory shape to the braid. Then, the braid may be drawn down to a reduced size for positioning in the vascular system. In alternative embodiments, the diameter of the stent portion in its expanded configuration may be 2.5, 3.0, 3.5, 4.0 mm or other dimensions as desired. This heat treatment imparts high resiliency and a geometrical shape memory to the wire forming the braided composite stent portion.

In further embodiments, the braid may be treated in the reduced size or in an intermediate size between the reduced and expanded size. In such further embodiments, the stent will tend to resume the size in which it was treated. These alternative embodiments may be preferred in certain circumstances.

The pick count of the braid is a factor in the amount of treatment and the distance of axial travel associated with the braided wire that forms the stent portion. (The pick count is the number of crossings down a single axial line of elements per inch. For purposes of this specification, the pick count may be determined at the braiding stage before the stent is treated, such as by heating). A smaller pick count provides for less travel which which in turn minimizes trauma to the vessel. In a preferred embodiment, a braid having a pick count of less than 16 is used. In a most preferred embodiment, a braid having a pick count of 12 is used.

In a most preferred embodiment, the braid of wires that comprise the stent portion is formed of fewer than 20 wire elements. In a preferred embodiment, the stent portion is formed of 8 wire elements. At the crossing locations of the wires, the wires preferably form an axially-directed angle of 90 degrees or less and more preferably form an acute, axially-directed angle. This provides the advantage of minimizing the amount of material used in the stent thereby enhancing perfusion therethrough.

As mentioned above, in a most preferred embodiment, the composite stent includes a coating on the wire braid that forms the stent portion. The coating material is preferably a polymeric material such as polyurethane, silicone, or other high modulus, high elongation polymers. In a most preferred embodiment, the coating is an aliphatic polyurethane. The coating encapsulates and adheres to the crossing points and individual wire elements that form the braid, thus allowing rotation of these crossing points through elongation of the polymer, but preventing translation of the crossing points by adherences to the wire stands. The coating is preferably applied after the braid has been appropriately treated in an expanded configuration to impart a resiliency and memory to the metal braid, as described above. The coating thereby further enhances the memory shape characteristics. The coating may be sprayed on or applied by other methods such as by dipping or by dispersion. In a preferred embodiment, the coating is approximately less than 0.002 inches in thickness and preferably less than 0.001 inches in thickness. The coating may be thicker in some areas such as proximate to wire crossings. In alternative embodiments, other means may be utilized to "tie together" wire crossovers to enhance braid integrity as well as to impart stabilized lifting and holding properties to the braid.

In the most preferred embodiment, the stent portion possesses both dynamic and static stability. Dynamic stability allows the stent portion to lift an intimal vessel flap or vasoconstriction. Static stability allows the stent portion to maintain the vessel lumen by holding up a flap constriction or a vasoconstriction or vasospasm once the stent portion is in its expanded configuration. With the composite stent portion comprised of Elgiloy wire coated with an aliphatic urethane, these properties are provided with relatively few wire elements thereby allowing for a high level of blood perfusion through the stent. Also, with the composite stent, the overall dimensions of the stent can be minimized thereby facilitating tracking of the stent device to the desired vessel location. Through the use of the composite stent with the wire braid of expanded geometry memory and the non-translatable wire crossings, the number of wires need to form the stent portion can be minimized while still providing the necessary stability to the stent to maintain vessel patency for extended periods of time.

With a composite stent of the materials as described above, the stent can "lift" up to three 120 gram forces applied radially to a portion of the stent at 120 degree intervals around the location. A stent according to this embodiment would therefore provide for the ability to maintain the vessel open during most occurrences of vasoconstriction or vasospasm.

When devices are designed for use within the coronary arterial system size becomes a very significant factor. Each 1/1000th of an inch is significant both because of the primary concern which is restriction of flow, but also because of the added stiffness that results when a composite of tubular layers are sandwiched together to form the actuator member. For this reason, in one alternative embodiment, wire of rectangular cross section (herein referred to as flat wire) are utilized. One size of wire to make a 2.0 mm stent is 0.003 inches. For a 2.5 mm stent, wire of a size of 0.003 to 0.0035 may be used. For a 3.0 and 3.5 mm stent, wire of either 0.0035 or 0.0040 should be used. From this, the advantage of using flat wire becomes apparent. For each of the stent sizes, added thickness due to the braid is detailed below.

| SIZE | WIRE SIZE | STACK UP HEIGHT DIAMETRAL |
|---|---|---|
| 2.0 | .0015 FLAT | .006 |
| 2.0 | .003 ROUND | .012 |
| 2.5 | .0015 FLAT | .006 |
| 2.5 | .003 ROUND | .012 |
|  | .0035 ROUND | .014 |
| 3.0 | .002 FLAT | .008 |
| 3.0 | .0035 ROUND | .014 |
|  | .004 ROUND | .016 |
| 3.5 | .002 FLAT | .008 |
| 3.5 | .0035 ROUND | .012 |
|  | .004 ROUND | .016 |

From the above, the significance of the use of flat wire can be appreciated. It may be seen that a large profile change results using flat wire as opposed to round wire. Additionally, the use of the larger flat wire results in devices that are considerably stiffer.

In this alternative embodiment, the braiding operation uses flat wire. In this embodiment, a 2.0 mm stent is constructed with a braid mesh network using stainless steel wire of rectangular cross section with a thickness of 0.001 inch×0.004 inch. In this embodiment, for a 2.5 mm stent the wire used is stainless steel wire with a rectangular cross section of 0.0015 inches in thickness and 0.004 inch in width. In this embodiment, the 3 mm stent is constructed with a stainless steel wire of rectangular cross section with 0.002 inch thickness and 0.004 inch width. A 3.5 mm stent is constructed with either a 0.002 inch thickness and 0.004 inch width, or a 0.002 inch thickness and 0.005 inch to 0.007 inch width.

The wires that are used for the braid of the stent portion can be fragile due to their small size and care should be exercised in the manufacturing process. This is particularly true for the smaller wires such as the 0.003 inch round or the 0.0008 to 0.0015 thickness flat wires.

In this embodiment, the wire used in each of the aforementioned braiding operations is 304 stainless steel in a spring temper. The specific wire used is the Hyten (TM) wire available from Fort Wayne Metals of Fort Wayne, Ind. Additionally, any one or more or and in an embodiment 2, 3, or 4 of the 8 wires that comprise the braid may be made of an alloy of 92% platinum and 8% tungsten for the purpose of providing radiopacity. These alloys may are commercially available from a number of sources, such as Sigmund Cohn Corp. of Mount Vernon, N.Y., or California Fine Wire of Grover City, Calif.

The braiding process of the present invention requires modification of a commercially available braiding machine to achieve the desired consistency and braid density. In this embodiment, for both the round and the flat wires, the braid pattern is composed of 8 wires. Braiding machines range in size from 16 carriers to 100 carriers. The braiding machine used for the manufacture of the stent described herein is a modified KoKobun SL-4-16 braider available from Wardwell Braiding Machine Co. of Rhode Island, NY. This same company also manufacturers a series of braiders under the New England Butt trade name. The braiders may be manufactured to accommodate 4, 6, 8, 10, 12, 16, or 24 bobbins in the machine groups defined as NE Butt #1, #2, or the B-11-8. These are all very small bench top versions that are used for small fibers or wire when fragile tensioning is required. The KoKobun is similar to the New England #2. The N E Butt B-9 which is a New England Butt #1 could conceivably be modified to make a 6 or a 5 wire braid which would may also be used for this application.

Machine modifications include the removal of 8 of the 16 carriages, as well as the installation of ultra light tensioning springs on the braider carriages. Additionally the tent angle (i.e. the angle with which the wires approach the central core on which the braid is being installed) normally is free to float up and down as the braiding wire position and rate equilibrate on the central core. For the application of flat wire, the wire may tend to get caught on other wires which are being applied in the opposing direction. The wires then would get flipped over every few linear inches of braid therefore making the segment unusable or incorporatable within the catheter. This problem may be eliminated by providing an angled guide made of a low friction material such as teflon and containing the angle for which the desired tent angle should be guided.

The size and density of the stent is controlled by three variables: the size of the central core to which the braid is being applied; the rate of advancement of the central core through the braid region; and the angular velocity of the braiding carriages. These variables relative to each other determine the "pick" (number of wire group intersections per inch) density of the braid pattern. These variables also determine the size of the stent that will be manufactured.

In this embodiment, a 2.0 mm stent is made on a central core with a size of 0.050 inches and a density of 10 per inch. When removed from the core the stent will spring from the I.D. of 0.055 to 2.0 mm and have a pick density of approximately of 7 to 15 per inch or approximately 0.14 to 0.07 inches between groups or 3.6 mm to 1.8 mm. The degree for which the stent expands when removed from the core depends on the pick density during the braiding operation.

The table below outlines the expanded pick densities for the individual stent configurations. The braiding machine used must be modified so that the take up velocity of the central core and the radial velocity may be adjusted very precisely to achieve the exact density required. Due to the addition of the guide, as explained above, the density of the braid will not be allowed to assume its own pattern density by climbing up and down the central core, but instead will assume the required density.

| size | core size | pic distance when expanded |
|---|---|---|
| 2.0 | .050 | 1.8 to 3.6 mm |
| 2.5 | .055 | 1.8 to 3.6 mm |
| 3.0 | .062 | 1.8 to 3.6 mm |
| 03.5 | .068 | 1.8 to 3.6 mm |

From the table, the desired density in this embodiment is obtained by placing the bridges 1.8 to 3.6 mm apart. As mentioned above and unlike a dilation device, an feature of the temporary stent is that it is highly perfusable. This is accomplished in part by minimizing the density of metal within the vessel which may restrict the blood flow both though the ends of the stent and also radially from the sides of the stent. This is important because frequently side branches to the blood vessel are contained in the stent region and flow must exit the stent to keep these side branches perfused. The area or size of the stent should be minimized to maximize perfusion while maintaining sufficient structural support for a flap or other damaged part of the vessel.

The stent portion should not only be perfusable to allow blood flow therethrough, but should also minimize surfaces upon which a thrombus might form. The vascular system is very active with respect to clot formation once a vessel has been damaged or subjected to other trauma such as during an angioplasty. Any device that is installed for more than a few minutes is susceptible to clot formation. Because in some embodiments, the temporary stent may be used for up to several days, it should also provide for minimization of clot formation.

One way the temporary stent minimizes clot formation is by preparation of the surfaces of the wires of the stent portion. The wires of the braid in this embodiment are made of rectangular wires braided into a 4, or 8 wire braid and rectangular wire may, by reason of the manufacturing processes, have edges that are very and/or sharp. The wire is made by initially drawing it through a die in order to form the specific size that is desired. During this process the temper of the spring may be modified by the cold work that is being induced into the wire from the forceful shaping of the wire. In the case of the HyTen 304 SS wire, the spring tempers are being achieved with pressures which are substantially greater than 300,000 psi. This spring temper is very desirable from the standpoint of imparting desirable properties to the stent. Specifically, the stent must be resilient to return from its initial contracted configuration to the full expanded state with only a minimal application of external force. The temper is relevant to the fabrication process and ultimately to the product performance.

The edges formed on the flat wire are rounded off. The method used to radius the corners of the flat wire is electropolishing which removes edges or protrusions of the material and passivates the metal without altering the bulk properties of the metal. The metal is left in a passive state by the electropolishing process and the metal is also highly resistant to corrosion.

Figures 9, 10:
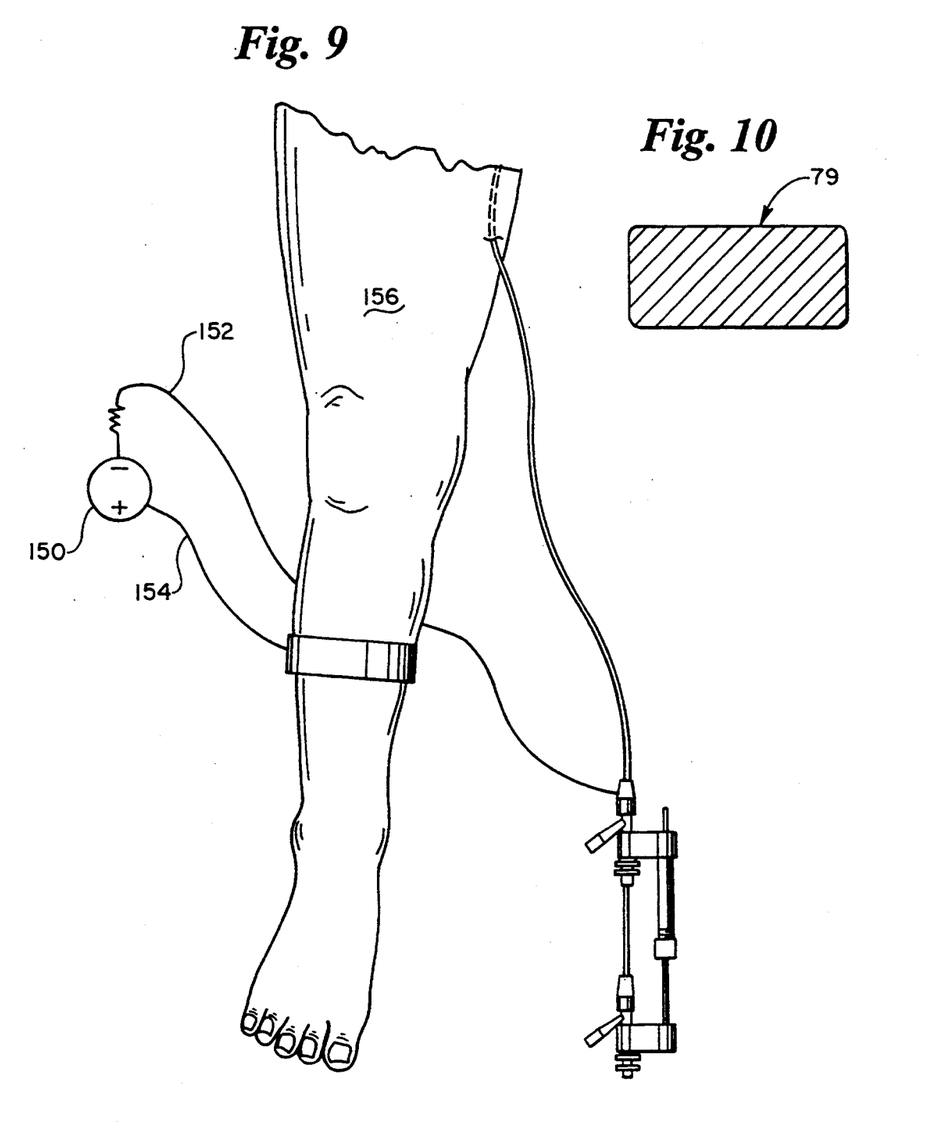
FIG. 9 depicts another embodiment of the present invention.
FIG. 10 is a cross section of an embodiment of a wire component along lines 10-10' of FIG. 2.

The electropolishing operation requires the use of an electrolytic fluid. This fluid must dissolve the products (formed on the work piece which in this case is the metal stent surface) by electro-chemical action. High current densities of 1000–5000 amps per square inch are maintained between the workpiece and a cathode. A DC power supply is used to provide the required power. The rate of removal is regulated by the current flow through the work piece. Corners or asperities extending from the surface of the work piece have a greater projected surface area/volume ratio than does the flat area. For this reason, material is removed from such regions at an accelerated rate. Further, this operation is ideal for smoothing the flat wire in the stent region and radiusing the corners which other wire would exhibit sufficient sharpness to potentially scrape the endothelial cells from the inside of the vessel thus promoting thrombus. After electropolishing, a flat wire 79 may possess a rounded cornered cross sectional profile, as depicted in FIG. 10.

The electropolishing operation may be performed as follows. The electropolishing solution should be selected which meets the operational requirements. An acidic solution should be selected which is compatible with the electro-chemical characteristics such that material may be removed without the production of carbides or other metal impurities on the surface which will result in corrosion. A direct current (DC) power supply is provided to provide the electromotive potential required to force the electrochemical sacrifice of metal from the surface. The positive (+) terminal (the anode) is attached to the workpiece, and the negative terminal is attached to a non-corrosive negative (−) terminal piece (the cathode).

The stainless steel wire requires a voltage of approximately 5 volts to perform the polishing operation. This voltage is dependent on the electropolishing solution being used as the electrolyte. The solution being used in this embodiment is a solution of phosphoric acid, citric acid, deionized water, and ethyl alcohol. The operation is performed at an elevated temperature in order to increase the rate of metal removal and provide for the smoothest possible surface. Other electrolytes are available additionally that are effective on the stainless steel. These solutions are frequently combinations of alcohol, multiple acids, and water. Sulfuric acid based solutions are frequently used in electropolishing of stainless steel. If other metals are used in whole or in part in the braid, e.g. platinum or tungsten, in order to provide for radiopacity, modifications to the method may be appropriate. Electropolishing solutions used on the platinum-tungsten material used on the rectangular wire used in the braid may be polished using a HF acid solution in the same manner as described above, or may be mechanically radiused prior to incorporation in the braid by winding the wire from spool to spool and passing over a sequence of polishing wheels. This may be preferred to avoid dealing with HF acid. Many of the other metals which alternatively will provide opacity under X-ray also are quite noble and require HF acid for polishing. The mechanical polishing method is preferable for these metals.

The ease of electropolishing the stainless steel and the smooth-burr free surface that is provided makes this the method over mechanical removal. It must be understood that mechanical removal is also possible and relatively easy with the stainless steel.

The stainless steel that is in the austenite alloys provides a self-repairing oxide film which prevents corrosion. Passivity may be diminished or lost by any process in which a localized oxygen withdrawal occurs by any means. Heating or chemical reactions are capable of relieving this oxygen. The passive state may be restored to the material by exposing the material to an oxidizing environment such as nitric acid. The passivation state may be altered during the electropolishing operation if the parameters are not closely controlled. The voltage driving the chemical reaction will affect the passive state of the remaining surface. In the case of the process utilizing the phosphoric acid solution the voltage and temperature at which the process is operated at is 80 degrees celsius and 5±0.25 volts. The specific solution composition is 757.6 cc/liter phosphoric acid, 181.8 cc/liter de-ionized water, 60.6 cc/liter denatured alcohol, and 303.0 grams/liter citric acid.

In addition to the electropolishing step described above, clot formation can further be minimized by the application of one or more antithrombogenic coatings. In this embodiment, the braided wires are coated in two layers with a silicone oil solution. The surface is treated twice to achieve complete surface coverage. Since the engagement of the braided stent section results in a relative movement of the individual wires with respect to each other, the stent region is coated in both an expanded and contracted configuration. The coating used in this embodiment is Dow Corning (R) MDX4-4159 silicone fluid. The coating may be applied in accordance with the instructions in Dow Corning Bulletin 51-599 (July 1982) for the MDX4-4159 silicone fluid which is incorporated herein by reference.

Although a braid is a presently preferred construction for the perfusable stent portion 14, other alternative embodiments may include a plurality of parallel wires forming a hollow cylindrical tube each wire substantially parallel to the axis of the hollow cylindrical tube. In this alternative construction, at the ends of the elongate hollow tube formed by the plurality of wires, each wire would include an oblique bend so that each wire could be connected to the actuator portion which is aligned with the axis of the hollow tube formed by the wires. Relative displacement between the ends of the wires would cause the oblique angles at the end of each wire to change thereby increasing or decreasing the diameter of the hollow tube to enable placement or removal of the stent from the vascular region of the patient's body. Other alternative constructions for the stent portion may also be provided.

In accordance with the present embodiment, it is presently preferred to utilize a temporary stent of a specific and selected expanded size suitable for the region of the vascular system in which it is intended to be installed. Accordingly, it is presently intended with this embodiment to utilize different sizes of stents where different expanded sizes are needed. Alternatively, where there is a need to apply a temporary stent in a small size vessel, instead of using a small size temporary stent, it is possible to utilize a large size temporary stent (i.e. one that is expandable to a large diameter) but to only expand it partially to an intermediate expanded diameter size. This could be accomplished by fixing the proximal ends of the actuator portion 18 and the inner elongate member 26 at an intermediate position between where the catheter is fully compressed and where it is fully expanded.

These dimensions provided above are intended as approximate and other sizes and dimensions may be selected and designed in accordance with the teachings of the present invention.

Figure 12:
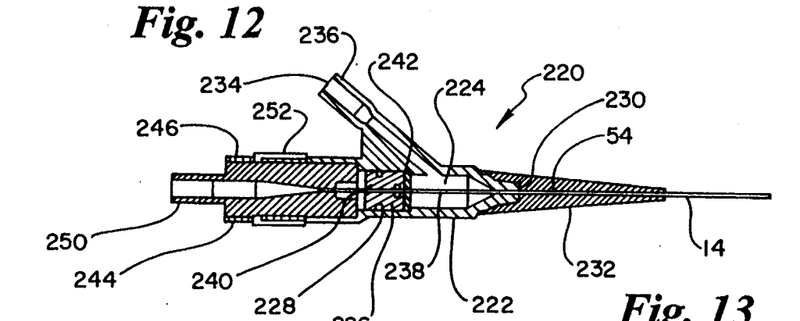
FIG. 12 is a cross section of a proximal portion of an embodiment of the present invention showing aspects of an embodiment of the manifold actuator assembly.
Figure 13:
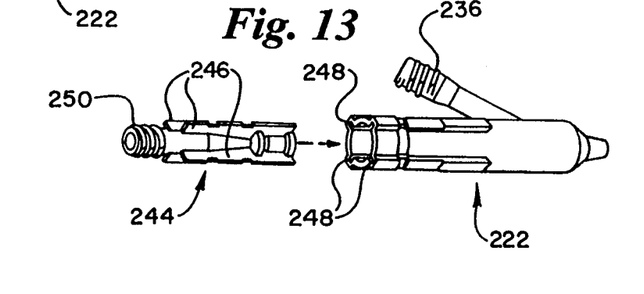
FIG. 13 is a perspective view of a portion of the manifold actuator assembly of FIG. 12.

In a most preferred embodiment, the temporary stent is operated by means of a manifold assembly 220, as depicted in FIGS. 12 and 13. Referring to FIG. 12, the manifold assembly 220 connects to the proximal end of the elongate member 14. The manifold assembly 220 includes a body portion 222 made of polycarbonate. The body portion 222 includes a reservoir 224 located internally thereto. An insert 226 is located in the body portion 222 and forms a distal end wall of the reservoir 224. A first O-ring 228 forms a seal between the insert 228 and the body portion 222.

The proximal portion of the outer catheter 54 communicates with the reservoir 224 via a distal opening 230 of the body portion 222. A strain relief member 232 fits over the proximal end of the outer catheter 54 at the location where it enters the distal opening 230 of the body portion 222. The strain relief member 232 is preferably conically shaped and made of pellethane. The proximal end of the outer catheter 54 terminates at the reservoir 224.

The body portion 222 also includes a port 234 communicating with the reservoir via a luer connection 236. Fluids such as medicines can be supplied via the port 234. Fluids supplied via the port 234 are thereby transported within the lumen of the outer catheter 54 in the annular region between the outer catheter 54 and the inner catheter 44 and discharged into the vessel at the distal termination of the outer catheter 54 at the proximal end of the stent portion 14.

A hypotube 238 is fixed to the outer diameter of the inner catheter 44. The hypotube 238 is preferably made of stainless steel. The proximal end of the hypotube 238 extends through an opening 240 through the insert 226. A second O-ring 242 fits between the hypotube 238 and the insert 226 to form a fluid tight seal.

The proximal end of the hypotube 238 terminates in an actuator member 244. Referring to FIG. 13, the actuator member 244 includes wings 246 that fit in corresponding grooves 248 of the body portion 222 so that the actuator member 244 can move longitudinally relative to the body portion 222 but not rotationally. The wings 246 also provide for structural support between the body portion 222 and the actuator member 244. The actuator member 244 includes a luer connection 250 on a distal end that communicates with the lumen of the inner catheter 44 via the lumen of the hypotube 238. In a preferred embodiment, the lumen of the inner catheter 44 is used for a guide wire so that the temporary stent can be positioned in the vascular system by means of an over-the-wire procedure. (In alternative embodiments, the temporary stent may use a fixed wire or a rapid exchange construction for positioning in the patient's vessel).

The actuator member 244 is sized and adapted for limited movement longitudinally in the body portion 222. Referring again to FIG. 12, a locking member 252, which in a preferred embodiment is a nut comprised of mating pieces of polycarbonate, fits over the proximal end of the body portion 222. The nut 252 includes a detente that engages one of the wings 246 of the actuator member 244 in order to lock it in either a fully extended or a fully retracted position with respect to the body portion 222. When the actuator member 244 is fully retracted proximally with respect to 10 the body portion 222, this corresponds to the atrest configuration of the stent portion in which the stent assumes its expanded configuration. When the actuator member 244 is fully extended distally with respect to the body portion 222, this corresponds to the contracted configuration of the stent such as when the stent is being positioned in or removed from the vessel.

Referring to FIG. 6, there is depicted the distal end of another embodiment of the present invention. The proximal end (not shown) could function similarly as in the first described embodiment. In this embodiment, a temporary stent 80 has a stent portion 82 and a actuator portion 84. The stent portion 82 is connected to the actuator portion 84 at a proximal end 86 of the stent portion 82. An inner elongate member 88 extends through the stent portion 82 and the actuator portion 84. As in the previous embodiment the inner elongate member 88 is connected to a distal end 90 of the stent portion 82. Also, as in the previous embodiment, the inner elongate member 88 may be moved relative to the actuator portion 84 to cause expansion and contraction of the stent portion 82.

In this embodiment, the inner elongate member 88 further includes a guidewire tip 92 that extends distally from the distal end 90 of the stent portion 82. The guide wire tip 92 is flexible and formable and includes a rounded portion 94. The guidewire tip 92 facilitates positioning the temporary stent 80 in the vascular system. In FIG. 4, the guidewire tip 92 is depicted having a curvature although it should be understood that the guidewire would normally be provided in a straightened position and that the curvature may be imparted by a physician prior to insertion into the vascular system of the patient in order to facilitate positioning of the stent. The guidewire tip 92 may assume a curvature such as depicted during its positioning in a tortuous vessel path. In this embodiment, the temporary stent 80 may be positioned by means of the guidewire tip 92 instead of over a separate guidewire that is located the inside an inner catheter (e.g. lumen 50 of inner catheter 44 in the first embodiment).

Figure 7:
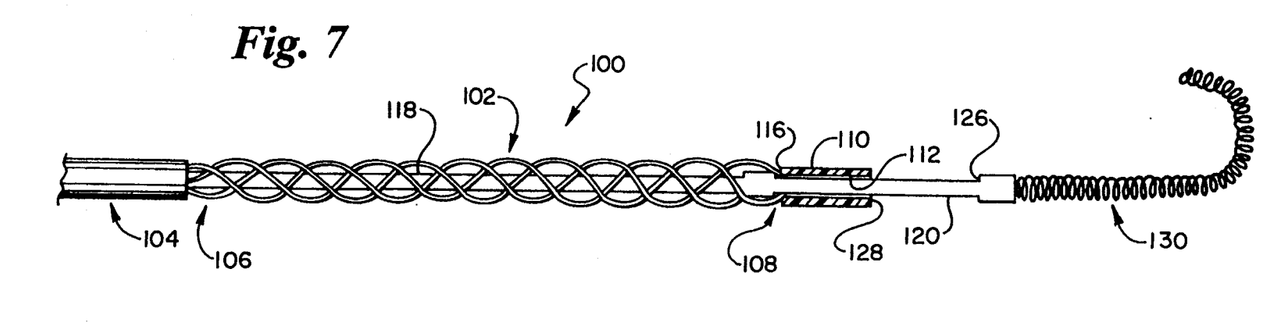
FIG. 7 depicts a distal portion of another embodiment of the present invention in a contracted configuration.
Figure 8:
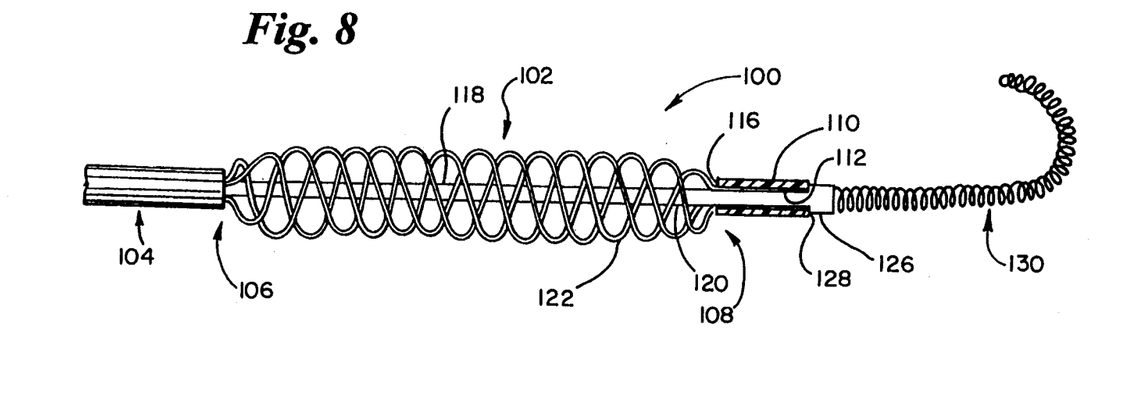
FIG. 8 depicts the distal portion of the embodiment shown in FIG. 7 in an expanded configuration.

Referring to FIGS. 7 and 8, there is depicted another embodiment of the present invention. In FIGS. 7 and 8, a temporary stent 100 includes a stent portion 102 and a actuator portion 104 connected to each other at a proximal end 106 of the stent portion 102. In this embodiment, a distal end 108 of the stent portion 102 includes a cylindrical shaft 110 having a cylindrical opening 112 therethrough. The cylindrical shaft 110 includes at least one bearing surface 116 thereupon. An inner elongate number 118 is located in the hollow tube of the formed by the stent portion 102 and extends proximally as in the previous embodiments. Unlike the previous embodiments, the inner elongate member 118 is not fixed to stent portion 102. Instead, the inner elongate portion 118 has a narrow distal portion 120 positioned to be slidingly received in the opening 112 of the shaft 110. A first shoulder 122 on the inner elongate member 118 is located to bear upon the surface 116 when the inner elongate member 118 is moved distally. The inner elongate member 118 also includes a second shoulder 126 formed distally of the narrow distal section 120. The second shoulder 126 is located to bear upon another surface 128 of the inner elongate member 118. Proximal movement of the inner elongate member 118 causes the shoulder 126 to bear upon the surface 128 causing expansion of the stent portion 102. As shown in FIG. 8, the second shoulder 126 may form part of a guide wire tip 130. However, other configurations for the tip are also suitable. With the embodiment of the invention depicted in FIGS. 7 and 8, limited axial movement of the inner elongate member 118 is provided which may be suitable and desirable for positioning and removal of the removable stent. As shown in FIGS. 7 and 8, the surfaces 116 and 128 and the shoulders 122 and 126 may be formed to prevent removal of the inner elongate member 118 from the actuator portion 104 and stent portion 102 although removability may be provided by alignment of the shoulders 106 with the bearing surface 128. As in the previously described embodiment, with this embodiment a separate guide wire is not required to position the temporary stent inside the vascular system.

As described above, because the temporary stent will be left in the vascular system for a period of time, the temporary stent should avoid or minimize clotting or platelet aggregation in and around the stent portion. Also, it is advantageous to reduce the tendency of the stent to permanently adhere to the inner surface of the vascular walls in order to facilitate removal of the stent. This may be accomplished by providing or imparting to the temporary stent properties that will minimize these tendencies.

In one alternative embodiment, the stent portion includes a coating of a slow release polymer having antithrombogenic properties. Such polymers include drugs such as urokinase, heparin, antithrombin III or other thrombon-resistive agents. The polymer used may be polyethylene or a polyolefin.

The natural surface charge that is present intrinsically on a material is considered to be a factor in the chain of successive events that results in the formation of mural thrombus on an artificial surface. Although, the blood coagulation cascade is complex and not fully understood, it is accepted that on an artificial surface, characteristics such as low surface energy (i.e. hydrophobic), and the electro-negativity of the surface affect the initial events that are important to subsequent reactions or events that result in the formation of thrombus. For this reason, in this embodiment, the surface is coated with a silicone oil solution which is of a low surface energy. Other alternative coatings that will provide relative thromboresistance include teflon, and pyrolytic carbon. While pyrolytic carbon has a relatively high surface energy of approximately 50 dyne/cm which is generally not considered thromboresistant, upon exposure to blood it has been observed to present a change to about 30 dyne/cm. This is considered to be thromboresistant and is thus a widely used material in coating of metal heart valves. The relative success of the stent in placement in vivo is dependent upon the ability to manipulate the surface characteristics to "tune" the device to the requirements that are present but not fully understood in the blood chemistry reactions.

Other methods may be used to provide this property. For example, the surface of the stent portion may effectively be charged and polarized to prevent the sequence of events that results in clot formation. By installing an external ground plane to the patient and placing a lead to the metal surface, the braid may be energized such that it is essentially an insulated capacitor which will provide the surface charge of desired magnitude, and polarity. The voltage level supplied to the wire is effectively additive to the natural negativity of the surface. The net potential may be effectively adjusted to a zero, positive, or negative charge. Referring to FIG. 9, a charge is imparted to the stent portion. The DC power supply 150 is located outside the vascular system. Only a small current is necessary (for example, less than 50 microamps). This could be provided by a small battery such as a watch battery. This would be sufficient to impart a charge to the stent portion to minimize the tendency for clotting materials to form on the stent portion. The polarity may be selected based upon consideration of factors, such as material, coating, medication, etc. A lead 152 is connected to the stent portion of the temporary stent and the other lead 154 is connected to the body 156 of the patient. As described above, the proximal end of the stainless steel braid comprising the stent portion could extend all the way to the proximal end of the outer catheter to form part of, or to connect to, lead 152. The braid may provide a pathway proximally to the manifold which provides an electrically conductive pathway so that a surface charge may be placed which in effect overrides the natural electronegative characteristics of the stainless steel metal surface from which the braid is formed. Alternatively, the wires that make up the stent portion may connect to a lead at a point proximally from the proximal end of the stent portion and the lead could extend proximally.

Additionally by providing a waveform polarizing function, the stent surface may be polarized with a time varying potential. The application of a high frequency current in the kilohertz to the megahertz range is a procedure that has been tested for healing of wounds.

The construction of the stent portion is designed to have a periodic surface contact with the wounded vessel, and a network for applying desired voltage, and polarities and frequencies to an intimate contact with the wounded vessel. The device may be constructed to apply current to the stent of 0 to 20 micro amp to the surface when an uncoated surface is used or when a noble coating such as gold or platinum is applied. Gold may be applied by standard vapor deposition process known as sputter coating, or by an electro-chemical plating process. platinum is normally electro-plated.

Another method for imparting a charge to the stent portion is by means of an RF signal. By this method, the proximal end of the stent portion will be connected to a RF source.

It is intended that the foregoing detailed description be regarded as illustrative rather than limiting and that it is understood that the following claims including all equivalents are intended to define the scope of the invention.

We claim:

1. A removable stent for temporarily supporting a region of a vessel in a body comprising:
    a composite stent portion comprised of:
        an elongate perfusable vessel supporting portion adapted to be configurable between a reduced size for placement in the vessel and removal therefrom and an expanded size for structurally supporting the vessel in the region; and
        perfusable end portions connected to and forming ends of said vessel supporting portion and adapted to allow fluid flow therethrough, and further in which said composite stent portion is comprised of:
        a plurality of wires forming an elongate hollow tubular braid, and
        a coating applied to said tubular braid to limit relative translation of one of said plurality of wires with respect to another of said plurality of wires at a location in said braid at which the one of said plurality of wires crosses the other of said plurality of wires; and
        an actuator portion having a proximal end extending out of the body and a distal end connected to said stent portion and operable by manipulation at said proximal end to configure said support portion into said reduced size and said expanded size.

2. The temporary stent of claim 1 in which said stent portion is comprised of a first set of wires helically wound in a first direction and a second set of wires helically wound in a second direction such that when said vessel supporting portion is in said expanded size, the wires of said first set form acute angles with the wires of said second set.

3. The temporary stent of claim 1 in which said stent portion is comprised of a plurality of wound wires forming a braid having a pick count of less than 16.

4. The temporary stent of claim 1 in which said stent portion is comprised of a plurality of wound wires forming a braid having a pick count of 12.

5. The temporary stent of claim 1 in which said stent portion is comprised of a plurality of wound wires of a diameter of approximately 0.002 to 0.0025 inches.

6. The stent of claim 1 in which said composite stent portion is comprised of:
    a plurality of helically wound wires forming an elongate hollow tube, and
    a coating applied to the plurality of helically wound wires.

7. The stent of claim 6 in which said coating is formed of a high modulus, high elongation polymeric material.

8. The temporary stent of claim 7 in which said polymeric coating is an aliphatic polyurethane.

9. The temporary stent of claim 6 in which said polymeric material is selected from a group consisting of: polyurethane and silicone.

10. The temporary stent of claim 6 in which said coating encapsulates and adheres to crossing points of said plurality of helically wound wires thereby allowing relative rotation of wires at said crossing points but preventing translation of the wires at said crossing points.

11. The temporary stent of claim 6 in which said coating is preferably applied to said plurality of helically wound wires after said plurality of wires has been treated to resume an expanded configuration.

12. The temporary stent of claim 6 in which said coating is less than approximately 0.002 inches in thickness.

13. A removable stent for temporarily supporting a region of a vessel in a body comprising:
    a stent portion comprised of:
        an elongate perfusable vessel supporting portion adapted to be configurable between a reduced size for placement in the vessel and removal therefrom and an expanded size for structurally supporting the vessel in the region said expanded size having a larger diameter than said reduced size; and
        perfusable end portions connected to and forming ends of said vessel supporting portion and adapted to allow fluid flow therethrough; and
        an actuator portion having a proximal end extending out of the body and a distal end connected to said stent portion and operable by manipulation at said proximal end to configure said support portion into said reduced size and said expanded size;
    and further in which said stent portion comprises a resilient material having a memory to assume said expanded size.

14. The temporary stent of claim 13 in which said stent portion is comprised of a plurality of wound wires of a material treatable to resume a desired configuration.

15. The temporary stent of claim 13 in which said stent portion is comprised of a plurality of wound wires of a treatable cobalt-chromium-nickel-molybdenum based alloy.

16. The temporary stent of claim 13 in which said stent portion is comprised of a plurality of wound wires selected from a group consisting of: elgiloy and MP35N.

17. The temporary stent of claim 13 in which said stent portion comprises a plurality of wound wires of a metal formed to resiliently return to a configuration conforming to said expanded size.

18. A removable stent for temporarily supporting a region of a vessel in a body comprising:
    a stent portion comprised of:
        an elongate perfusable vessel supporting portion adapted to be configurable between a reduced size for placement in the vessel and removal therefrom and an expanded size for structurally supporting the vessel in the region; and perfusable end portions connected to and forming ends of said vessel supporting portion and adapted to allow fluid flow therethrough; and an actuator portion having a proximal end extending out of the body and a distal end connected to said stent portion and operable by manipulation at said proximal end to configure said support portion into said reduced size and said expanded size, said actuator portion comprising:

a first elongate member comprising an elongate catheter tube connected to said proximal end of said stent portion, and a second elongate member slidably disposed in a lumen of said first elongate member and extending to and operable to move said distal end of said stent portion with respect to said proximal end of said stent portion;

a first marker connected at approximately the distal end of said stent portion;

a second marker connected at approximately the proximal end of said stent portion, whereby the length of said stent portion can be determined by observation of said first and said second markers.

19. The temporary stent of claim 18 further including:
a third marker connected to said second elongate member in a portion corresponding to the stent portion, whereby the relative positions of said first and second elongate members and thereby the size of said vessel supporting portion can be determined by observation of the position of said third marker relative to said first and second markers.

20. The temporary stent of claim 19 in which said third marker is connected to said second elongate member at a location such that when said vessel supporting portion is in said expanded size said third marker is proximate to said second marker.

21. The temporary stent of claim 18 in which said markers are made of platinum with 10% iridium.

22. A removable stent for temporarily supporting a region of a vessel in a body comprising:
a composite stent portion comprised of:
an elongate perfusable vessel supporting portion adapted to be configurable between a reduced size for placement in the vessel and removal therefrom and an expanded size for structurally supporting the vessel in the region; and
perfusable end portions connected to and forming ends of said vessel supporting portion and adapted to allow fluid flow therethrough; and
an actuator portion having a proximal end extending out of the body and a distal end connected to said stent portion and operable by manipulation at said proximal end to configure said support portion into said reduced size and said expanded size, said actuator portion comprising:
a first elongate member comprising an elongate catheter tube connected to said proximal end of said stent portion,
a second elongate member slidably disposed in a lumen of said first elongate member and extending to and operable to move said distal end of said stent portion with respect to said proximal end of said stent portion, and
a lubricous coating located between said second elongate member and said first elongate member.

23. The temporary stent of claim 22 in which said second elongate member further includes said lubricous coating on at least one surface thereof.

24. The temporary stent of claim 23 in which said lubricious coating is located on an inner surface of said second elongate member.

25. The temporary stent of claim 23 in which said lubricious coating is located on an outer surface of said second elongate member.

26. The temporary stent of claim 23 in which said lubricious coating is selected from a group consisting of: a hydrophilic coating, paralyene, teflon, and silicone.

27. The temporary stent of claim 22 in which said first elongate member further includes said lubricous coating on at least one surface thereof.

28. The temporary stent of claim 27 in which said lubricious coating is located on an inner surface of said first elongate member.

29. The temporary stent of claim 27 in which said lubricious coating is located on an outer surface of said first elongate member.

30. The temporary stent of claim 27 in which said lubricious coating is selected from a group consisting of: a hydrophilic coating, paralyene, teflon, and silicone.

31. A method of stabilizing a patient's vessel during an occurrence or during a time when there is the potential for an occurrence of a restriction to blood flow through the vessel from a vasoconstriction, vasospasm, or similar condition at a location in the vessel, comprising the steps of:
positioning a temporary stent into the patient's vessel with a vessel supporting portion of the temporary stent in the vessel at the location and an actuator portion of the temporary stent having a distal portion connected to the vessel supporting portion and a proximal portion extending out of the patient's vessel;
manipulating the vessel supporting portion from the proximal portion of the actuator portion to cause the vessel supporting portion to change from a reduced size suitable for positioning of the temporary stent in the patient's vessel to an expanded size suitable for supporting the patient's vessel during an occurrence or during a time when there is the potential for an occurrence of a restriction to blood flow through the vessel from a vasoconstriction, vasospasm, or similar condition;
maintaining said vessel supporting portion in said expanded size while permitting blood perfusion through distal and proximal ends of the vessel supporting portion;
manipulating the vessel supporting portion from the proximal portion of the actuator portion to cause the vessel supporting portion to change from said expanded size to said a reduced size;
withdrawing the temporary stent after the condition or potential of a condition of a vasoconstriction, vasospasm, or similar condition has passed.

32. The method of claim 31 further comprising the step of:
during at least a portion of said vessel maintaining step, administering medicines from the proximal end of the actuator portion to a proximal portion of the vessel supporting portion via a lumen of an outer catheter member of the actuator portion.

33. The method of claim 32 in which the positioning step further comprises:
maintaining an outer catheter connected to a proximal end of the vessel supporting portion in tension with respect to an inner catheter located internally to said outer catheter and connected to a distal end of the vessel supporting portion to maintain said vessel supporting portion in the reduced size as the vessel supporting portion is advanced through the patient's vascular system; and in which the manipulating step further comprises:

reducing the tension maintained on the outer catheter so that said vessel supporting portion resumes an expanded size.

34. A removable stent for temporarily supporting a region of a vessel in a body comprising:
  (a) a stent portion comprised of:
    (i) an elongate perfusable vessel supporting portion adapted to be configurable between a reduced size for placement in the vessel and removal therefrom and an expanded size for structurally supporting the vessel in the region; and
    (ii) perfusable end portions connected to and forming ends of said vessel supporting portion and adapted to allow fluid flow therethrough,
  and further in which said stent portion is comprised of:
    a plurality of wires forming an elongate hollow tubular braid,
  and further in which relative translation of one of said plurality of wires with respect to another of said plurality of wires at locations in said braid at which one of said plurality of wires crosses another of said plurality of wires is limited; and
  (b) an actuator portion having a proximal end extending out of the body and a distal end connected to said stent portion and operable by manipulation at said proximal end to configure said support portion into said reduced size and said expanded size.

35. A removable stent for temporarily supporting a region of a vessel in a body comprising:
  (a) a stent portion comprised of:
    (i) an elongate perfusable vessel supporting portion adapted to be configurable between a reduced size for placement in the vessel and removal therefrom and an expanded size for structurally supporting the vessel in the region; and
    (ii) perfusable end portions connected to and forming ends of said vessel supporting portion and adapted to allow fluid flow therethrough,
  and further in which said stent portion is comprised of:
    a plurality of wires forming an elongate hollow tubular braid having sufficient structural strength for supporting three radially compressive forces on the order of 120 grams in order to support the region of the vessel; and
  (b) an actuator portion having a proximal end extending out of the body and a distal end connected to said stent portion and operable by manipulation at said proximal end to configure said supporting portion into said reduced size and said expanded size.

* * * * *